United States Patent
Limaye (10) Patent No.: US 12,409,278 B2
(45) Date of Patent: Sep. 9, 2025

(54) DEVICE FOR FACILITATING NEEDLE INJECTION

(71) Applicant: Becton, Dickinson and Company, Franklin Lakes, NJ (US)

(72) Inventor: Amit Limaye, Wayne, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 163 days.

(21) Appl. No.: 16/768,635

(22) PCT Filed: Dec. 19, 2018

(86) PCT No.: PCT/US2018/066401
§ 371 (c)(1),
(2) Date: May 29, 2020

(87) PCT Pub. No.: WO2019/126268
PCT Pub. Date: Jun. 27, 2019

(65) Prior Publication Data
US 2021/0170114 A1    Jun. 10, 2021

Related U.S. Application Data

(60) Provisional application No. 62/608,981, filed on Dec. 21, 2017.

(51) Int. Cl.
*A61M 5/42* (2006.01)
*A61M 5/32* (2006.01)

(52) U.S. Cl.
CPC .............. *A61M 5/427* (2013.01); *A61M 5/32* (2013.01); *A61M 2205/587* (2013.01); *A61M 2205/6072* (2013.01)

(58) Field of Classification Search
CPC .......... A61M 5/427; A61M 5/42; A61M 5/32; A61M 5/3287; A61M 5/46;
(Continued)

(56) References Cited

U.S. PATENT DOCUMENTS 2,238,323 A * 4/1941 Hollingsworth ........ A61M 5/46
604/117
5,437,640 A     8/1995 Schwab
(Continued)

FOREIGN PATENT DOCUMENTS

EP         2886148 A1     6/2015
JP      2015532180 A     11/2015
(Continued)

OTHER PUBLICATIONS

Japanese Patent Application No. 2020-532883 Official Notice of Rejection.

*Primary Examiner* — Kevin C Sirmons
*Assistant Examiner* — Alexandra E Lalonde
(74) *Attorney, Agent, or Firm* — Dickinson Wright, PLLC (57) ABSTRACT

A device (25) is provided to aid in needle insertion of an injector, such as a safety pen needle (10). The device (25) includes a housing (30) having a mounting surface (38) configured to contact a skin surface (78), and a hole (46) configured to receive the injector (10), wherein the hole (46) is configured allow the injector (10) to bottom out on the hole (46) to aid in the needle insertion. An LED (70) may also be provided to illuminate the housing (30) for use in low light conditions.

13 Claims, 5 Drawing Sheets

(58) Field of Classification Search
CPC .... A61M 2205/587; A61M 2205/6072; A61M 2005/1585; A61M 2005/3139; A61M 2005/1586; A61M 2005/3267; A61M 5/158; A61M 5/425; A61M 5/002; A61M 5/14244; A61M 5/3134; A61M 25/02; A61B 5/15016; A61B 5/150748; A61B 2017/3407; A61B 2017/3411; A61B 17/3403; A61J 1/2065

See application file for complete search history.

(56) References Cited

U.S. PATENT DOCUMENTS

| | | | |
|---|---|---|---|
| 5,578,014 | A | 11/1996 | Erez et al. |
| 7,645,264 | B2 | 1/2010 | Marsh et al. |
| 9,636,468 | B2 | 5/2017 | Tromborg |
| 2001/0044606 | A1* | 11/2001 | Inkpen ................ A61M 5/3287 604/181 |
| 2005/0203466 | A1* | 9/2005 | Hommann .......... A61M 5/3158 604/240 |
| 2009/0082734 | A1* | 3/2009 | Walters ................ A61J 1/1406 604/165.01 |
| 2009/0259179 | A1* | 10/2009 | Hillios .................... A61M 5/46 604/110 |
| 2010/0217105 | A1 | 8/2010 | Yodfat et al. |
| 2013/0096502 | A1* | 4/2013 | Kawamoto ............ A61M 5/42 604/117 |
| 2014/0039658 | A1* | 2/2014 | Bangera ............. A61B 17/3403 700/98 |
| 2015/0258284 | A1 | 9/2015 | Fenster et al. |
| 2016/0228652 | A1* | 8/2016 | Cabiri ............... A61M 5/14248 |
| 2016/0235915 | A1* | 8/2016 | Cabiri ................. A61M 5/3287 |
| 2016/0339186 | A1 | 11/2016 | Hagy et al. |
| 2016/0367766 | A1* | 12/2016 | Baker ................... A61M 5/427 |
| 2017/0095622 | A1* | 4/2017 | Bral .................. A61B 5/15105 |
| 2017/0232205 | A1 | 8/2017 | Cowe et al. |
| 2017/0357776 | A1* | 12/2017 | Baker ................ G09B 19/0053 |
| 2018/0264202 | A1* | 9/2018 | Kim .................... A61M 5/3287 |

FOREIGN PATENT DOCUMENTS

| | | |
|---|---|---|
| JP | 2017514577 A | 6/2017 |
| WO | 0061209 | 10/2000 |
| WO | 2017048772 A1 | 3/2017 |

* cited by examiner

DEVICE FOR FACILITATING NEEDLE INJECTION

CROSS-REFERENCE TO RELATED APPLICATION

This application claims the benefit under 35 U.S.C. § 119(e) of U.S. Provisional Application No. 62/608,981, filed on Dec. 21, 2017, which is incorporated herein by reference in its entirety.

FIELD OF THE INVENTION

The present invention relates generally to needle injections, especially needle injections performed with safety pen needles.

BACKGROUND OF THE INVENTION

Safety pen needles are well known in the art to be used similar to medical injectors and other injectors, particularly medication delivery pen injectors. Shielding of a used needle before and after injection is provided by such devices. However, due to the presence of the shield, it can be difficult for a health care professional to confirm needle exposure or needle injection, as well as provide safety activation.

Figure 1:
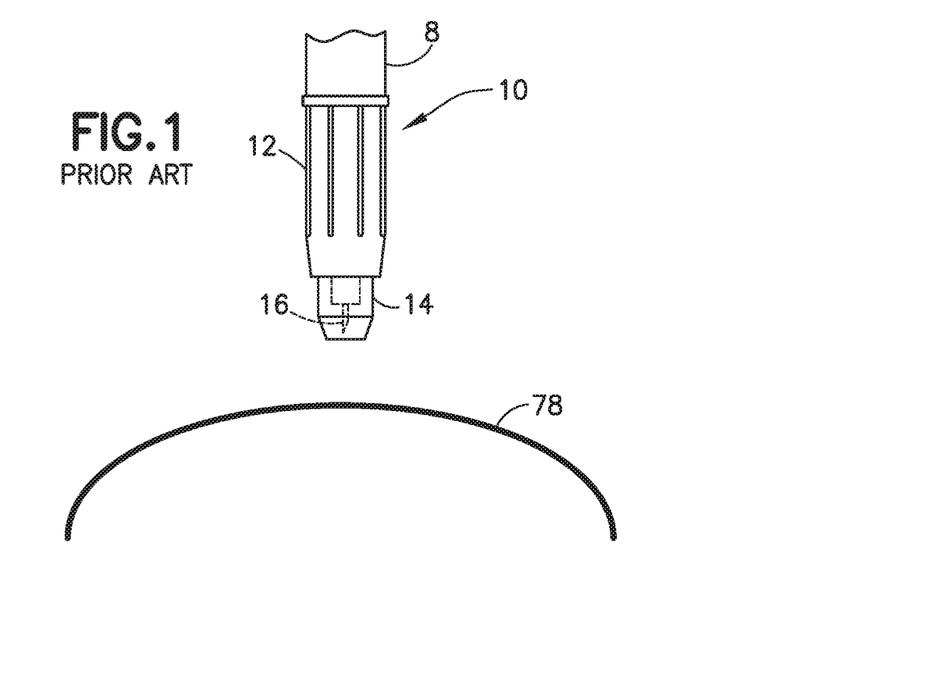
FIG. 1 is a side perspective view of a safety pen needle of the prior art and a skin of a patient.
Figure 2:
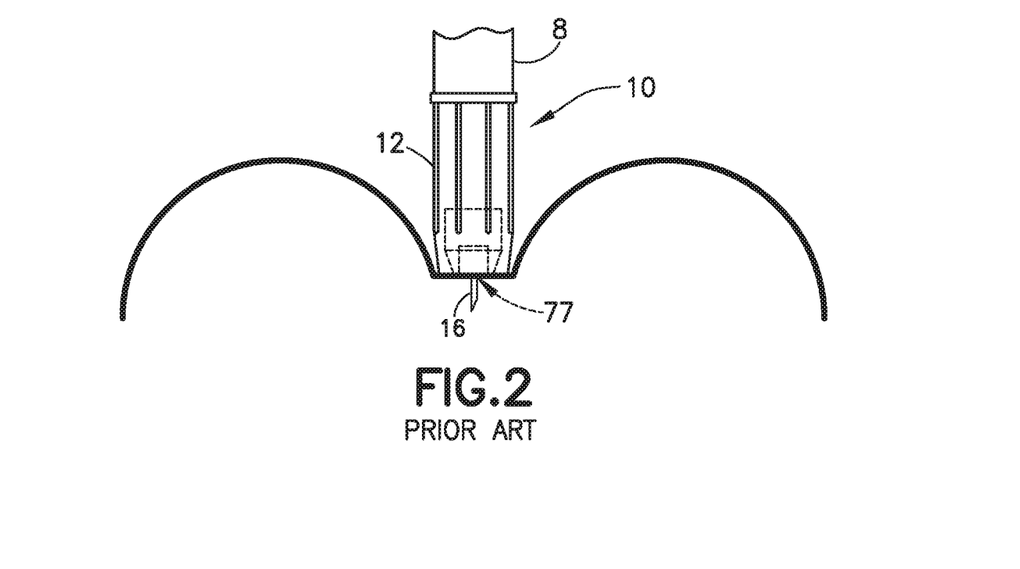
FIG. 2 is a side perspective view of a needle of a safety pen needle of the prior art being inserted in the skin of the patient.

As illustrated in FIGS. 1 and 2, it can be difficult to confirm subcutaneous needle injection when the safety pen needle is used on a patient with a high body mass index (BMI) or having soft skin. Dimpling of the skin during injection, for example, can create problems such as varying the injection force, causing bruising from excessive pressure, activating the safety mechanism prematurely, and causing angled needle insertion.

Conventional pen needles can also experience problems when the skin dimples during injection. These problems include varying the injection force, causing bruising from excessive pressure and causing angled needle insertion.

SUMMARY OF THE INVENTION

It is an aspect of the present invention to provide a device to aid in pen needle injection. Such a device automatically flattens the skin of a patient, especially those with high BMI or soft skin. The device substantially self-centers the pen needle, reduces excessive force, minimizes the likelihood of premature activation, and provides for a more reliable and accurate subcutaneous needle insertion process.

The foregoing and/or other aspects of the present invention can be achieved by providing a device configured to aid in needle insertion by an injector, the device including a housing having a mounting surface configured to contact a skin surface, a hole configured to engage the injector and a taper substantially concentric with the hole to improve engagement with the injector.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

As described above, FIG. 1 illustrates a medication delivery pen 8 attached to a single-use safety pen needle 10 of the prior art including a housing 12, a movable needle shield 14 forming part of a safety mechanism, and a needle cannula 16. The safety pen needle 10 is being injected into the skin surface 78 of a patient. Problems can sometimes arise with the use of safety pen needles 10. As illustrated in FIG. 2, for patients with soft skin or a high body mass index (BMI), the pressure applied to the safety pen needle 10 can cause dimpling 77 of the skin surface 78. This dimpling 77 can create an uncontrolled and variable injection force.

Specifically, it sometimes cannot be accurately and consistently determined with how much force or how hard a healthcare practitioner should press the safety pen needle 10 against the skin surface 78. As a result, the safety mechanism of the safety pen needle 10 can be prematurely activated by excessive injection force. As further described below, once the safety mechanism is activated and subsequently locked, the safety pen needle 10 is no longer operable. Alternatively, the dimpling 77 can make it difficult for the safety shield 14 to fully retract and activate the safety mechanism. In this case, if the safety mechanism does not activate, the safely pen needle 10 can potentially be reused, which is not desired. Finally, excessive injection force and applied pressure from the healthcare practitioner may also create bruising on the skin surface 78 of the patient.

Dimpling 77 of the skin surface 78 can also create angled insertion of the needle 16 of the safety pen needle 10. Since a flat positioning on the skin surface 78 is difficult to achieve, many times the needle 16 of the safety pen needle 10 is not inserted in a substantially perpendicular direction to the skin surface 78. Accordingly, the healthcare practitioner is unsure if the safety pen needle 10 is inserted into the desired subcutaneous region of the skin. If the safety pen needle 10 is inserted beyond the subcutaneous region of the skin, the muscle of the patient may be undesirably accessed. If the safely pen needle 10 is inserted and placed in the dermis or epidermis region of the skin instead of the subcutaneous region, the patient may not experience proper medication effectiveness.

Dimpling 77 of the skin surface 78 can make it difficult to achieve consistent depth of deposition of medicament into the subcutaneous region of the skin. In other words, injection repeatability and reducing injection variability are difficult to achieve when dimpling 77 of the skin surface 78 occurs during needle injection.

Angled insertion of the needle 16 in the safety pen needle 10 can cause premature activation of the safety mechanism. Further, if the safety pen needle 10 does not engage the skin surface 78 in a substantially perpendicular direction, an accidental needle stick injury to the healthcare practitioner is possible.

Conventional pen needles can also experience similar problems when the skin dimples during injection. These problems can include varying the injection force, causing variable depth of deposition of the medication, bruising from excessive pressure, and causing angled needle insertion.

To avoid the problems associated with dimpling 77 of the skin surface 78, healthcare practitioners typically stretch the skin surface 78 to create a flat surface. Alternately, healthcare practitioners pinch the skin surface 78 of the patient to access the subcutaneous layer of the skin. However, these methods are unreliable and inconsistent ways to achieve proper needle depth and isolate the subcutaneous layer. Also, bruises may form due to the manipulation of the skin surface 78.

In view of the challenges in the prior art as described above, a device 25, as illustrated in FIG. 3, is provided to aid in needle insertion by an injector, such as a safety pen needle 10. The specific device 25 shown is intended for use with a safety pen needle 10 having a retractable shield 14, but embodiments of the device 25 can be used with any generally available safety pen needles (FIGS. 3-8) and with conventional pen needles (FIGS. 9 and 10), as well as with injectors other than pen needles, such as syringes.

Figure 3:
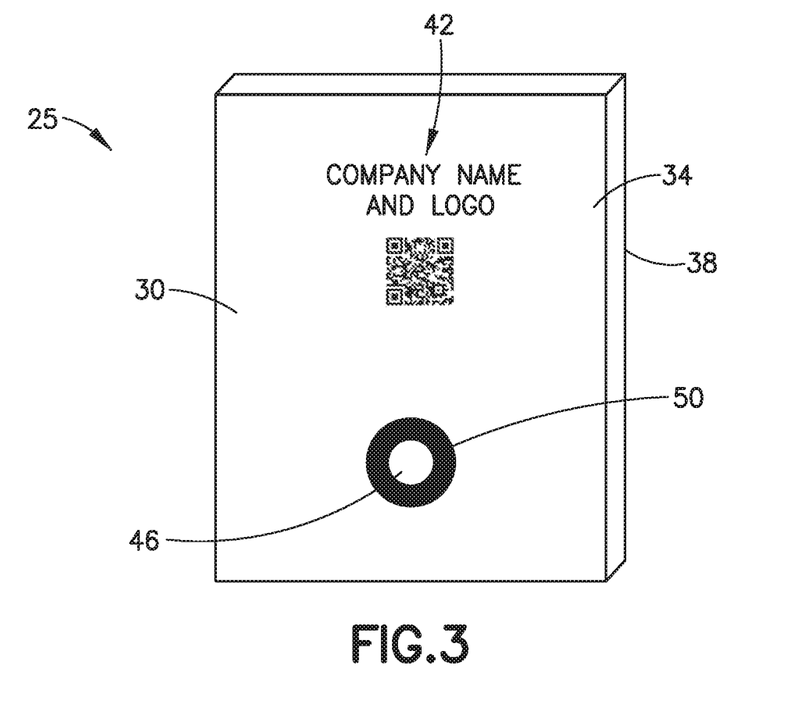
FIG. 3 is a front perspective view of a first exemplary embodiment of a device to aid in pen needle injection.
Figure 4:
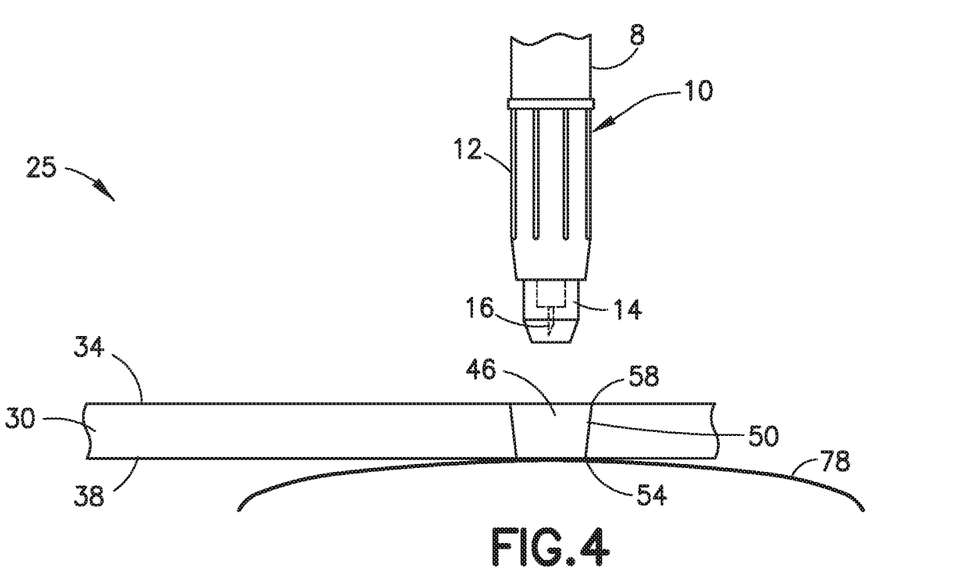
FIG. 4 is a cross-sectional view of the device of FIG. 3 configured to engage a safety pen needle and mounted on the skin surface.
Figure 5:
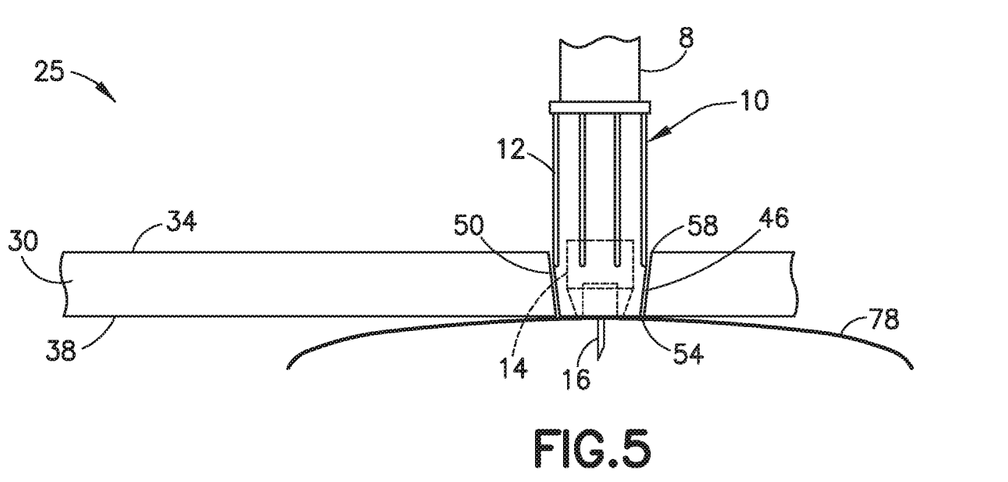
FIG. 5 is a cross-sectional view of the device of FIG. 3 engaging the safety pen needle and the pen needle piercing the skin of the patient.

As illustrated in FIGS. 3-5, the device 25 includes a housing 30. Preferably, the housing 30 is made of a polymer that is transparent, or translucent and white or light in color, to allow for illumination as further described below. The housing 30 is preferably rectangular in shape, and is similar in size to a credit card. Preferably, the housing 30 is substantially shaped as a flat credit card. However, other shapes and sizes are contemplated to improve ergonomics. For example, the housing 30 can include finger grips, provide easier handling and be contoured in shape. The shape and size of the housing 30 can vary so long as an appropriate surface area is provided to engage the skin surface 78 to achieve the benefits described herein.

The housing 30 includes a top surface 34 and a bottom surface 38. Preferably, both the top and bottom surfaces 34, 38 are substantially flat and smooth. Alternately, the top and/or bottom surfaces 34, 38 can be designed to include different contours such as a smooth convex or smooth concave surface. Such contours can provide a better user experience, for example, a tactile feedback identifying adequate or improved skin contact.

The top surface 34 has an information marking 42 including at least one of a brand or trademark, a company name and logo, patient information, teaching instructions, awareness information, an image, a barcode, and a scannable QR code (shown). In one embodiment, the patient or healthcare practitioner can use a smartphone or mobile device camera to scan the QR code which is linked to a website that provides information for proper operation of the safety pen needle 10 and the device 25.

The bottom surface 38 provides a mounting surface and is configured to contact the skin surface 78 of the patient. FIG. 4 illustrates the device 25 mounted on the skin surface 78 of the patient prior to needle insertion. FIG. 5 illustrates the device 25 mounted on the skin surface 78 of the patient when the needle 16 of the safety pen needle 10 is inserted. As noted, the bottom surface 38 is substantially flat and smooth to advantageously create a flat skin surface 78 for needle insertion of the safety pen needle 10.

FIGS. 3-5 also illustrate the housing 30 having a hole 46 that is tapered 50 and configured to engage the safety pen needle 10. The taper 50 is substantially concentric with the hole 46. The taper 50 and the hole 46 have a different color than the rest of the housing 30. Preferably, the housing 30 is not tinted or is of a lighter color and can be transparent, translucent or opaque, while the taper 50 and the hole 46 is a darker color. The selected colors advantageously allow the taper 50 and the hole 46 to be more conspicuous on the housing 30.

The taper 50 includes a first diameter 54 and a second diameter 58. The first diameter 54 of the taper 50 is disposed on the bottom surface 38 of the housing 30. The second diameter 58 of the taper 50 is disposed on the top surface 34 of the housing 30. The second diameter is larger than the first diameter.

The second diameter 58 of the taper 50 is preferably sized to be slightly larger than an outer diameter of the housing 12 of the safety pen needle 10. The first diameter 54 of the taper 50 is preferably sized to be slightly smaller than an outer diameter of the housing 12 of the safety pen needle 10. In other words, the taper 50 is configured to substantially correspond to a tapered outer surface of the safety pen needle 10, but allows for ease of insertion. In this manner, the depth of insertion of the safety pen needle 10 is advantageously controlled.

Specifically, when the safety pen needle 10 is inserted into the taper 50, a distal end of the housing 12 of the safety pen needle 10 initially enters via a loose fit. Subsequently, the distal end of the housing 12 of the safety pen needle 10 bottoms out either loosely, with a tight fit or a snug fit, for example, and in the latter case is secured to the first diameter 54 of the device 25. As a result, the distal end of the housing 12 of the safety pen needle 10 is flush with the mounting surface 38 of the device 25. Accordingly, during use, the bottom surface 38 of the device 25 provide a larger and more equally distributed surface pressure on the skin surface 78 for improved needle insertion.

In another embodiment, the taper 50 includes a first diameter 54, a second diameter 58 and a third diameter (not shown). The second diameter 58 is the same as in the above embodiment. The first diameter 54 is smaller than the outer diameter of the housing 12 of the safety pen needle 10 but large enough for the safety shield 14 to enter. The third diameter creates a stepped surface below the taper 50 and between the first and second diameters 54, 58. The third diameter is sized slightly larger than the outer diameter of the housing 12 of the safety pen needle 10. In operation, the safety pen needle 10 is inserted into the second diameter 58 of the taper 50 and bottoms on the stepped surface at the third diameter. Although the housing 12 of the safety pen needle 10 is not flush with the mounting surface 38, the thickness of the stepped surface is known and so the depth of insertion can be controlled in this manner as well.

Additionally, as illustrated in FIGS. 3-5, the hole 46 and taper 50 substantially self-centers the safety pen needle 10 in the device 25 upon engagement. The hole 46 also advantageously provides for substantially perpendicular needle entry of the safety pen needle 10 upon engagement to the skin surface 78 of the patient.

The device 25 is intended to be easy to clean by using common cleaning methods and materials such as isopropyl alcohol, bleach, and other cleaning agents. To provide this advantage, the device 25 is designed to include, for example, no shallow crevices and no areas conducive for dirt to collect.

FIGS. 4 and 5 illustrate the operation of the safety pen needle 10 and the device 25. In FIG. 4, the safety pen needle 10 has not yet been used. Thus, the safety mechanism is not locked. The device 25 is placed on the skin surface 78 of the patient. Specifically, the mounting surface 38 contacts the skin surface 78 via a pressing force applied by the patient or healthcare practitioner.

Subsequently, as illustrated in FIG. 5, the safety pen needle 10 is inserted into the hole 46 of the device 25. The safety shield 14 is retracted inside the housing 12 of the safety pen needle 10 to activate the safety mechanism. At the same time, the needle 16 of the safety pen needle 10 is inserted into the skin surface 78 of the patient and medicament is delivered.

After medication delivery is complete, the safety pen needle 10 is removed from the device 25. As the safety pen needle 10 is removed, the safety mechanism extends from the housing 12 to cover the needle 16. The safety mechanism locks to permanently shield the needle 16 and prevent the safety pen needle 10 from being used again.

In addition to substantially self-centering the safety pen needle 10 and substantially perpendicularly entering the skin as described above, the device 25 provides additional benefits not realized by the prior art. The flat mounting surface 38 of the device 25 provides automatic flattening of the skin surface 78 at the target site. This is especially helpful for high BMI patients or patients with soft skin. The healthcare practitioner can apply a pressing force to the device 25 directly and/or through the safety pen needle 10 to cause the device 25 to contact and flatten the skin surface 78.

Flattening the skin surface 78 advantageously allows for a consistent depth of deposition of medicament into the subcutaneous region of the skin. Accordingly, injections are repeatable and there is less injection variability.

Because of the relatively large surface area of the device 25, a range of forces can be advantageously applied by the healthcare practitioner and still ensure that the needle 16 of the safety pen needle 10 enters into the subcutaneous layer of the skin of the patient. As a result, the use of the device 25 to assist needle insertion of the safety pen needle 10 provides better performance than manually stretching and flattening the skin or pinching the skin.

When the needle 16 of the safety pen needle 10 is substantially perpendicularly inserted into the skin of the patient, it is much less likely that the safety mechanism will be inadvertently or prematurely activated. Thus, it will be less likely that the safety mechanism will undesirably lock the safety pen needle 10 before use. In view of the above, when the device 25 is used for assistance, the patient and the healthcare practitioner gain more confidence in using the safety pen needle 10 and the results are more reliable.

Figure 6:
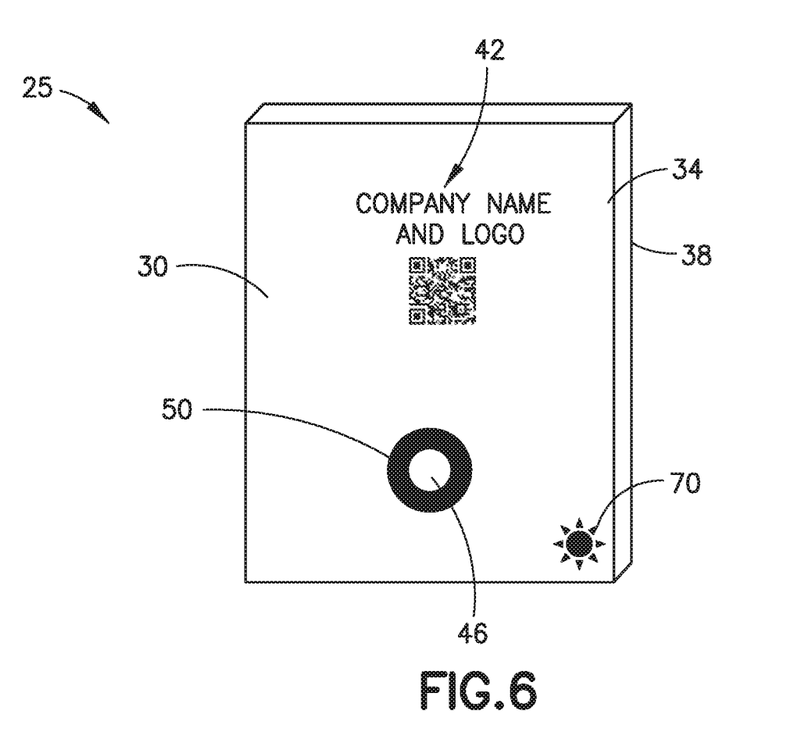
FIG. 6 is a front perspective view of a second exemplary embodiment of the device of FIG. 2 with an LED.
Figure 7:
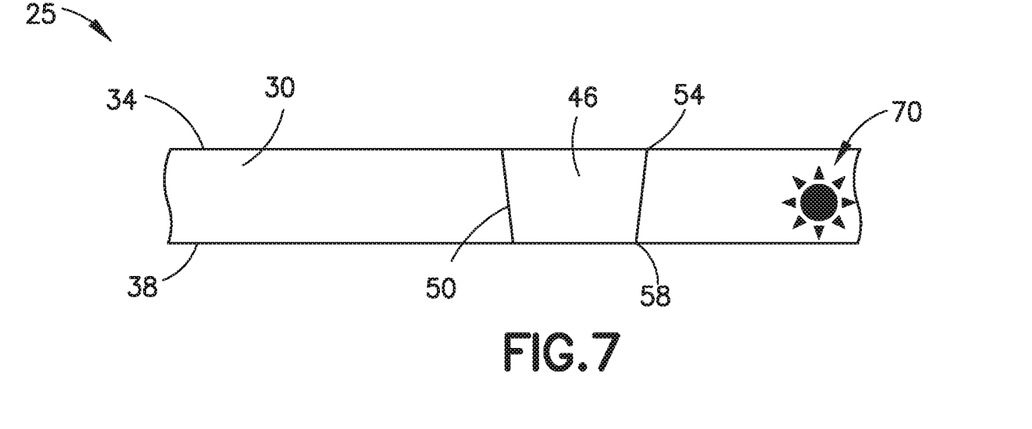
FIG. 7 is a cross-sectional view of the device of FIG. 6.
Figure 8:
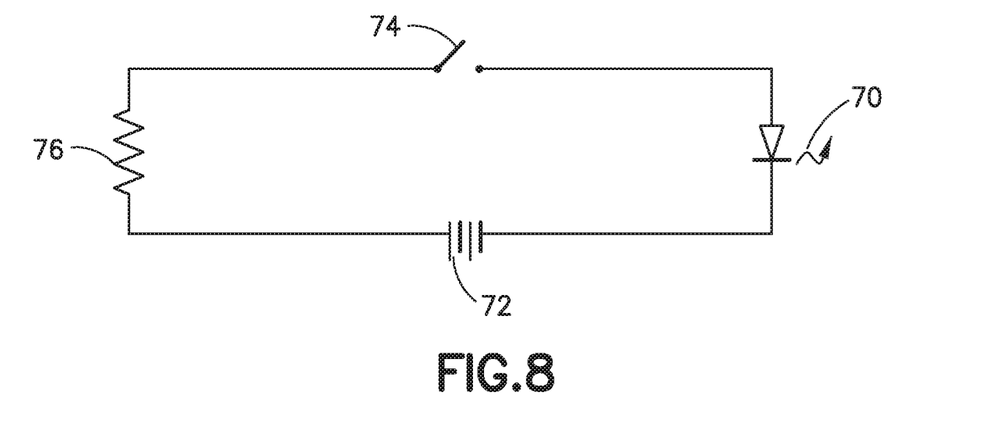
FIG. 8 is a schematic diagram of an electrical circuit of the device of FIG. 6.

FIGS. 6-8 illustrate a second exemplary embodiment of the device 25. This embodiment is similar to the embodiment described above, but further includes a light emitting diode (LED) 70 that illuminates the transparent or translucent housing 30. The LED 70 is disposed in the housing 30 and adjacent to the hole 46. As illustrated in the electrical diagram of FIG. 8, the LED 70 is connected to a battery 72 through a switch 74 and resistor 76 for selective activation and deactivation. The switch 74 can be provided as a button or membrane switch on the top surface 34 of the housing 30, or on a side of the housing 30 adjacent to a location where the device 25 is gripped while in use, so that the switch can be easily operated by the user.

The LED 70 advantageously illuminates the housing 30 to better visualize the taper 50 and the hole 46 of the device 25. As described above, the different colors of the housing 30 with respect to the taper 50 and the hole 46 in combination with the LED 70 advantageously allow the taper 50 and the hole 46 to be even more conspicuous on the housing 30. Thus, the healthcare practitioner and the patient can better see the self-centering mechanism of the device 25 to use the safety pen needle 10 most effectively.

Also, the LED 70 advantageously aids the healthcare practitioner and the patient for using the device 25 and the safety pen needle 10 in low light conditions. These low light conditions are typical in hospital and outpatient care facilities.

Figure 9:
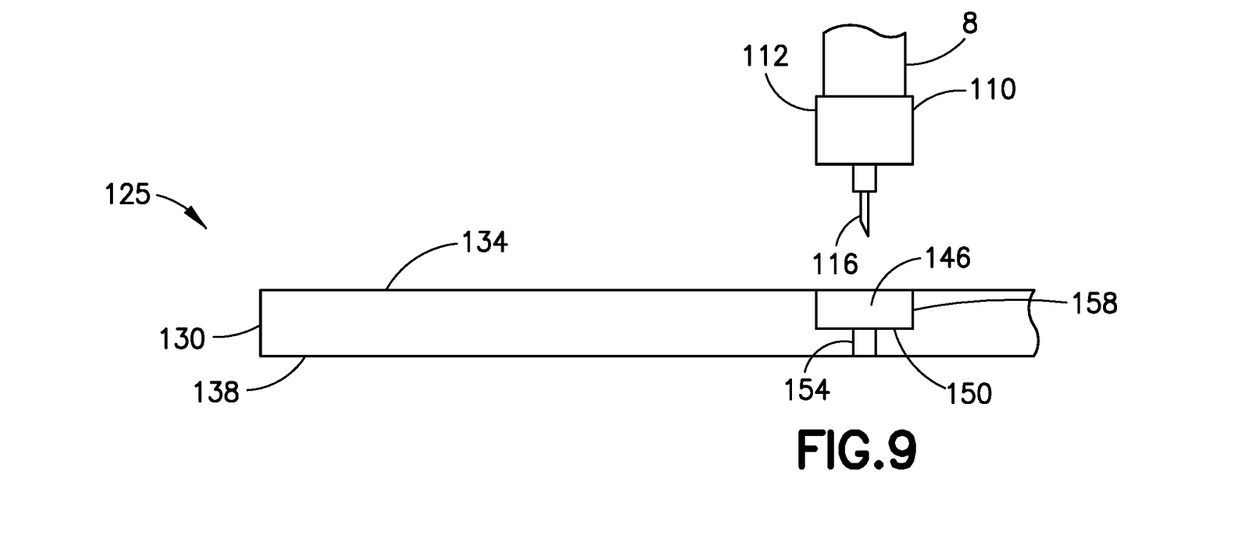
FIG. 9 is a cross-sectional view of a third exemplary embodiment of a medication delivery pen having a pen needle configured to engage a device.
Figure 10:
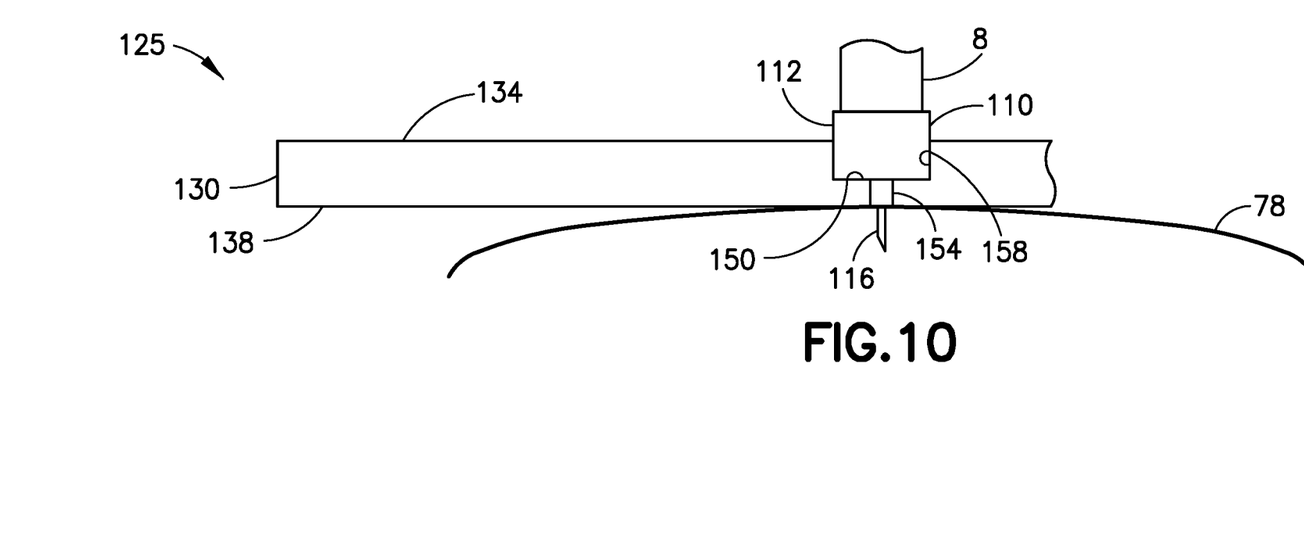
FIG. 10 is a cross-sectional view of the device of FIG. 9 engaging the pen needle and piercing the skin of the patient.

FIGS. 9 and 10 illustrate a third embodiment of a device 125 for use with a conventional pen needle 110 attached to a medication delivery pen 8. The pen needle 110 includes a hub 112 having a main body on a proximal end of the hub 112 and a boss disposed at a distal end of the hub 112, and a needle cannula 116. The needle cannula 116 is fixed to the boss at the distal end of the hub 112.

The device 125 is similar to the embodiment described above but is configured to be used with a conventional pen needle 110. The device 125 includes a housing 130 having a top surface 134 and a bottom surface 138 as similarly described above. The device 125 includes a hole 146 having a first diameter 154 and a second diameter 158. The first and second diameters 154, 158 are substantially concentric. The first diameter 154 is sized to be greater than the outer diameter of the needle 116 and greater than the outer diameter of the boss of the hub 112 but smaller than the outer diameter of the main body of the hub 112. The first diameter 154 opens into a stepped surface 150. The stepped surface 150 is a recessed surface from the top surface 134 at the second diameter 158. The second diameter 158 is sized to be slightly larger than the outer diameter of the main body of the hub 112 to guide the pen needle 110 into the hole 146. In another embodiment (not shown), the second diameter 158 is tapered as in the first embodiment to facilitate insertion of the pen needle 110 into the device 125.

During operation, the medication delivery pen 8 is held so that the pen needle 110 is inserted into the hole 146 of the device 125. A distal end of the main body of the hub 112 contacts and bottoms onto the stepped surface 150 of the device 125. At the same time, the needle cannula 116 is inserted into the skin of the patient. The applied force from the user travels through the medication delivery pen 8 and to the distal end of the main body of the hub 112. The stepped surface 150 receives the applied force and distributes the force across the bottom surface 138 of the device 125. Accordingly, the device 125 provides many of the advantages described above, mainly to prevent dimpling of the skin surface, provide a substantially smooth surface for the needle cannula 116 to be inserted in a substantially perpendicular direction, reduce injection force variability, and reduce injection deposition depth variability.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A system including a safety pen and a device configured to aid in insertion of a needle of the safety pen, the device comprising:
    a housing including
        a mounting surface configured to contact a skin surface;
        a top surface disposed opposite of the mounting surface, the top surface being a top most surface of the device and the top surface comprises an external surface of the device, and
        a hole configured to receive the safety pen, a full depth of the hole being tapered, the hole extending directly from the top surface to the mounting surface; wherein
    the hole is configured to allow the safety pen to bottom out in the hole to position the safety pen for the insertion of the needle of the safety pen; and
    the safety pen comprises a safety mechanism cooperating with the needle of the safety pen, the safety mechanism includes a retractable shield, the retractable shield configured to surround the needle of the safety pen prior to the insertion of the needle of the safety pen, the retractable shield configured to contact the skin surface to retract the retractable shield, the safety mechanism is configured to shield the needle of the safety pen after use and lock the retractable shield to prevent reuse of the needle of the safety pen.

2. The system of claim 1, wherein the housing is transparent or translucent.

3. The system of claim 1, wherein the housing is substantially rectangular in shape.

4. The system of claim 1, wherein the mounting surface is substantially flat.

5. The system of claim 1, wherein the housing has an information marking including at least one of a brand or a trademark, a company name and a logo, patient information, teaching instructions, awareness information, an image, a barcode, and a scannable QR code.

6. The system of claim 5, wherein the information marking is disposed on the top surface.

7. The system of claim 1, wherein the top surface is substantially flat.

8. The system of claim 1, wherein
    a first diameter of the hole that is tapered is disposed on the mounting surface of the housing;
    a second diameter of the hole that is tapered is disposed on the top surface; and
    the second diameter is larger than the first diameter.

9. The system of claim 1, wherein the hole that is tapered substantially corresponds to a tapered outer surface of the safety pen.

10. The system of claim 1, wherein the housing is configured so that a bottom distal surface of the safety pen is flush with the mounting surface of the housing when the safety pen bottoms out in the hole.

11. The system of claim 1, wherein the housing includes an LED that illuminates the housing to aid in insertion of the safety pen in the hole.

12. The system of claim 11, wherein the LED is adjacent to the hole of the housing.

13. The system of claim 1, wherein
    premature activation of the safety mechanism is avoided; and
    the needle of the safety pen includes a hub having a main body, a boss extending from the main body, and the needle of the safety pen fixed to the boss.

* * * * *